United States Patent [19]

Velenyi et al.

[11] Patent Number: 4,663,479
[45] Date of Patent: May 5, 1987

[54] PREPARATION OF ALIPHATIC CARBOXYLIC ACIDS AND ALDEHYDES BY UPGRADING ALPHA-HYDROXYCARBOXYLIC ACIDS

[75] Inventors: Louis J. Velenyi, Lyndhurst; Serge R. Dolhyj, Parma, both of Ohio

[73] Assignee: The Standard Oil Company, Cleveland, Ohio

[21] Appl. No.: 657,442

[22] Filed: Oct. 4, 1984

[51] Int. Cl.$^4$ ............................................. C07C 101/30
[52] U.S. Cl. ..................................... 562/525; 562/524; 562/599; 562/606; 562/607; 568/484
[58] Field of Search ............... 562/609, 606, 607, 525, 562/524, 599; 260/413; 568/484

[56] References Cited

U.S. PATENT DOCUMENTS 4,320,229  3/1982  Young ................................. 568/484
4,328,373  5/1982  Strojny et al. ...................... 568/484

OTHER PUBLICATIONS

Srivastava, Proceedings of the National Academy of Sciences India, 1969, vol. XXXIX, Section-A, Part III, pp. 273-278.

Semichon et al., (Comp. Rend., 194, 1827-9 (1932) Chemical Abstracts, 26:4302-4303, 1932.

Nakagawa et al., Chemical Abstracts, 61:1789c, 1964.

*Primary Examiner*—Werren B. Lone
*Attorney, Agent, or Firm*—Teresan W. Gilbert; Joseph G. Curatolo; Larry W. Evans

[57] ABSTRACT

A process for converting α-hydroxycarboxylic acids to hydroxy free aliphatic carboxylic acids and aldehydes in the presence of a catalyst of the formula:

$$M_a M'_b O_x$$

wherein
M is at least one of an element selected from Group IB, VIB, IVA; and
M' is at least one of an element selected from Groups IA, IIA, IVA, VA, VIA, VIIIB, VB.

7 Claims, No Drawings

PREPARATION OF ALIPHATIC CARBOXYLIC ACIDS AND ALDEHYDES BY UPGRADING ALPHA-HYDROXYCARBOXYLIC ACIDS

BACKGROUND OF THE INVENTION

The present invention relates to catalysts and a novel process for the upgrading α-hydroxycarboxylic acids to more useful and valuable chemical compounds. In another aspect, the invention relates to a novel process for selectively converting lactic acids to useful products such as propanoic acid, acetic acid and acetaldehyde.

Catalyst systems similar to the one employed in this inventive process are used to decarboxylate alkyl aromatic compounds. For example, U.S. Pat. No. 4,319,066 teaches a process of preparing alkenyl aromatic compounds by employing a decarboxylation catalyst. U.S. Pat. No. 4,393,260 teaches a process for the preparation of cyclohexanyl compounds by employing a decarboxylation catalyst. These processes do not include α-hydroxycarboxylic acids substrates as are employed in this inventive process.

Lactic acid, a reactant of the inventive process, is a hydroxycarboxylic acid that is an inexpensive material that can be manufactured synthetically or by fermentation. Hydroxycarboxylic acids contain two functional groups, both a carboxy and a hydroxyl group. Lactic acid is a useful intermediate chemical compound that can be converted into more valuable industrial products such as propanoic acid, acetic acid, acetaldehyde, acrylic acid, ethanol, propanol, etc.

The inventive process converts α-hydroxycarboxylic acids to hydroxy free aliphatic acids and aldehydes. Methods for producing the products of the inventive process and in particular the manufacture of propanoic acid, acetic acid and acetaldehyde are described below.

The major method of manufacturing propanoic acid is by the oxo-process or hydrocarbon-oxidation process. The oxo-process is the reaction of ethylene and carbon monoxide under reductive conditions to produce propionaldehyde which is further oxidized to the acid. The hydrocarbon-oxidation route is the liquid-phase oxidation of propane, butane, mixed paraffins and paraffin wax to the acid. A further process is the direct oxidation of 1-propanol with nitric acid.

The methods of producing acetic acid have shifted from natural fermentation processes to synthetic processes. Natural fermentation processes include alcohol fermentation and destructive distillation of hard wood. Principle synthetic processes employed include oxidation of acetaldehyde, direct oxidation of ethanol, hydrocarbon-oxidation and methanol-carbon monoxide process.

The major method of producing acetaldehyde is by liquid-phase oxidation of ethylene. Further commercial processes are by partial oxidation of ethyl alcohol and the hydration of acetylene. Acetaldehyde is also formed as a coproduct in the vapor phase oxidation of saturated hydrocarbons. A more recent process for producing acetaldehyde is by the direct conversion of synthesis gas in the presence of a rhodium catalyst.

For various reasons, none of the above processes are entirely satisfactory. Further, propanoic acid, acetic acid and acetaldehyde are not typically produced from lactic acid. Consequently, there exists an interest in developing new processes for upgrading lactic acid to more valuable chemical compounds. Thus, it is the object of this invention to provide a novel process for the conversion of α-hydroxycarboxylic acids to selectively form aliphatic acids, aldehydes, ketones and alcohols. It is another object of this invention to produce valuable chemicals, such as propanoic acid, acetic acid and acetaldehyde.

This and other objects of the invention will become apparent in the description of the invention and the examples which follow.

SUMMARY OF THE INVENTION

According to this invention, α-hydroxycarboxylic acids are upgraded to more valuable chemicals by a process comprising contacting an α-hydroxycarboxylic acid with the catalyst of Formula (I):

$$M_a M'_b O_x \qquad (I)$$

wherein

M is at least one element selected from Group IB, VIB, IVA of the Periodic Table;

M' is at least one of an element selected from Group IA, IIA, IVA, VA, VIA, VIIIB or VB of the Periodic Table;

with the proviso that when M is selected from Group IVA, then M' is not selected from Group IVA; and wherein a is 0.1 to 1;

b is 0.0 to 0.5; and x is a number sufficient to satisfy the valence requirements of the other elements present.

The process is characterized by a high conversion of the starting material and a good selectivity to the hydroxy free aliphatic carboxylic acids and aldehydes.

DETAILED DESCRIPTION OF THE INVENTION

The starting materials of this invention are α-hydroxycarboxylic acids which may be represented by the formula:

R—CHOH—COOH wherein R is a hydrogen or an alkyl having from 1 to 4 carbon atoms.

Typically, the α-hydroxycarboxylic acid reactants of this invention include α-hydroxyisobutyric acid, lactic acid, α-hydroxypentanoic acid and α-hydroxyhexanoic acid. A particularly preferred starting material is lactic acid.

When the α-hydroxycarboxylic acid is lactic acid and is converted in accordance with this invention, the aliphatic carboxylic acids and aldehydes that are produced are propanoic acid, acetic acid, acetaldehyde or a combination of the three.

Generally, the starting materials are in the gaseous phase, however, they also may be in the liquid phase. The starting materials may contain various impurities such as oxygenated compounds, e.g. oxygenated hydrocarbons and water. When the starting material is lactic acid, it should be at least 10 percent pure chemical, with a 30 to 60 percent purity preferred.

CATALYST

The catalysts used in the inventive process are compounds of Formula I:

$$M_a M'_b O_x \qquad (I)$$

wherein

M is at least one element selected from Group IB, VIB, IVA of the Periodic Table; and M' is at least one of an element selected from Group IA, IIA, IVA, VA, VIA, VIIIB or VB;

with the proviso that when M is selected from Group IVA, then M' is not selected from Group IVA; and wherein a is 0.1 to 1;

b is 0.0 to 0.5; and x is a number sufficient to satisfy the valence requirements of the other elements present.

Preferably M is Cu, Mo, Sn or a combination of Cu, Mo and Sn. Preferred elements in the M' group are Na, K, Rb, Mg, Ca, P, Sb, Bi, Te, Ge, Sn, Pb, Fe, Co, Ni, V, and Nb.

As taught by Formula I, certain of the components can be combinations of two or more elements, e.g. M can be a combination of Cu, Mo and Sn. In such circumstances, the subscript value represents the sum of the elements, e.g. for M the sum of Cu, Mo and Sn is equal to a, which is 0.1 to 1. The individual components of the subscript value, e.g. subscript values for Cu, Mo and Sn can vary to convenience.

These cataysts can be used either in their 100 percent active form or diluted with other materials, e.g. loaded onto a carrier. If diluted, generally any carrier can be used such as silica, alumina, silica-alumina, titania, Zeolite, zirconia and the like all being exemplary. Silica-alumina is the preferred carrier. If a support is used, the catalyst composition is generally present in an amount of at least about 5 weight percent based on the combined weight of the support and the catalytic composition, and preferably in an amount of at least 30 weight percent.

The catalytic composition of this invention can be prepared by any one of a number of different known methods, the particular method employed being a matter of convenience. Typically the catalysts are prepared by mixing the appropriate catalyst ingredients in the proper proportions in an aqueous mixture, drying the resulting slurry optionally with a reducing agent and calcining the product. The ingredients can be added in any order during the preparation.

The ingredients employed can be the oxides, halides, nitrates, acetates, oxalates or other salts of the particular metals or elements added. If a support is used, the material comprising the support may be incorporated into the catalyst along with the other ingredients or the catalytic composition can be coated and/or impregnated onto or into an inert core. After the catalyst ingredients have been combined to form an aqueous slurry, the slurry is evaporated to dryness and the dried solid obtained is heated in the presence of air, oxygen or nitrogen at a temperature between about 300° C. and 600° C., preferably 350° to 450° C. to form the catalyst. When the catalyst is heated in the presence of nitrogen, the oxide form of the catalyst occurs by thermal decomposition of the nitrate. This calcination can take place outside the catalytic reactor or an in situ activation can be utilized. Other methods of preparation are broadly taught in the art.

The exact structure or elemental arrangement of the catalyst is not known but the components are present in the form of their oxides or oxide complexes. However, compositions of Formula I are known not to be a mere physical mixture of their components but rather unique entities where the individual components are chemically and/or physically bonded to one another.

PROCESS CONDITIONS

Heterogeneous catalysis is used in this invention, i.e. at reaction conditions the reactant is a gas or liquid, preferably a gas, while the catalyst is a solid. Any temperature and pressure which the reactant is a gas or liquid can be employed. However, practical consideration such as economy, convenience, reactants, catalysts, and product degradation are limitation upon the maximum temperature that can be used. When the reactant is in a gaseous phase, the temperature employed is usually between 200° C. and 600° C. Preferably the temperature employed is between 300° C. to 400° C. and optimally the temperature employed is between 325° C. to 375° C. When the reactant is in the liquid phase, for example, in an autoclave environment, the temperature employed is between 150° C. and 300° C. Reaction pressure is unimportant and relates primarily to temperature. It can vary from subatmospheric to superatmospheric, with atmospheric pressure being preferred.

If the reactant is a gas at reaction conditions, it can be used by itself or diluted with a relatively inert gas and/or water. Representative diluent gases include nitrogen, argon, helium, carbon dioxide, steam, and the like. Likewise, if the reactant is a liquid at reaction conditions, it can be used either alone or with a diluent, such as mixed hexanes and heptanes, cyclohexane, benzene, water and the like. If the reactant is a solid at room temperature, it is usually solubilized with a suitable solvent, such as mixed hexanes and heptanes, cyclohexane, benzene, water, alcohol and the like, before exposure to the catalyst at reaction conditions.

Typically, the catalyst is employed in a fixed and/or fluid-bed reactor where the reactant is passed over or through the catalyst.

Contact or residence time can also vary widely, depending upon such variables as the reactant, catalyst, reactor, temperature, and pressure. Typically when the reactant is a gas at reaction conditions, contact time ranges from 0.5 to 10 seconds, with the preferred contact time between about 1 and 5 seconds and optimum contact time is about 4.2 seconds. When the reactant is in the liquid phase, in an autoclave environment, the reaction time is between 10 minutes and 5 hours.

PRODUCTS

The products produced by this invention are aliphatic hydroxy free carboxylic acids, aldehydes and alcohols. When the reactant is latic acid, the products of the reaction are mainly propanoic acid, acetic acid and/or acetaldehyde. The amount and combination of the products formed depends on the composition of the M and M' elements of the catalyst employed. By-products of this process include carbon monoxide, carbon dioxide, methane, ethane, and other hydrocarbons or olefins. The by-products are easily separated from the desired products by techniques such as physical separation or distillation. The aliphatic carboxylic acids and aldehydes produced by this invention are useful chemicals themselves and as intermediates to produce other chemicals. Propanoic acid finds use in the production of esters, salts, polymer products and specialty chemicals. Acetic acid is useful in the manufacture of various acetates, plastics, pharmaceuticals and dyes. Acetaldehydes find use as important chemical intermediates and in the production of perfumes and synthetic flavor additives to food.

SPECIFIC EMBODIMENT

The following examples are illustrative embodiments of this invention. Per pass conversion (ppc) and selectivity based on carbon were calculated using the following equations:

$$\text{Percent } ppc = \frac{\text{Moles of product formed}}{\text{Moles of reactant fed}} \times 100$$

$$\text{Selectivity} = \frac{\text{Moles of product formed}}{\text{Moles of reactant reacted}} \times 100$$

EXAMPLE 1

A catalyst consisting of 30% $Mo_5Cu_4SnO_x$, 52.5% $SiO_2$, 17.5% $Al_2O_3$ was prepared by dissolving 31.94 g of $Cu(CH_3COO)_2H_2O$ and 1600 ml of distilled water to yield a clear blue solution. To this solution was added 35.0 g of molybdenum trioxide in the form of ammonium heptamolybdate, causing the clear blue solution to turn cloudy and a light green precipitate to form. The mixture was brought to boiling. To this mixture was then added 6.02 g of stannic oxide and 202 g of 41% colloidal silica sol and 27.7 g of Dispal M alumina. The resulting mixture was then boiled and evaporated over the course of 1½ hours to thick, light green paste, and then dried over night at about 100° C. The resulting hard, light green material was calcined for 2½ hours at about 380° C. in a muffle furnace. The final product was a light green material which was ground to a 10-30 mesh U.S. standard.

The catalyst was charged to a 20 cc down flow, fixed-bed reactor. A feed of lactic acid was fed to the reactor together with steam and nitrogen, at about 350° C., at atmospheric pressure and with a contact time of 4.2 seconds. The feed had a ratio of 1 mole lactic acid, 14.5 moles water and 6.7 moles of nitrogen for Example 1 and 1 mole lactic acid, 12.3 moles water and 6.5 moles of nitrogen for all the other examples. The off-gas was passed through a cold aqueous trap where the liquid products were retained. The liquid products were then quantitatively analyzed using a gas chromatograph. Product results are reported in Table 1.

EXAMPLE 2

The procedure of Example 1 was repeated except that a catalyst with the composition of 30% $Mo_5Cu_4O_x$, 52.5% $SiO_2$, 17.5% $Al_2O_3$ was used. The catalyst was prepared by dissolving 6.36 g of $Cu(CH_3COO)_2H_2O$ in 800 cc of distilled water to yield a clear blue solution. To this solution was added 17.5 g of molybdenum trioxide in the form of ammonium heptamolybdate resulting in a light green precipitate. This mixture was boiled for a half hour after which 88.0 g of 41% Nalco silica sol and 12.1 g of Dispal M alumina were added. The resulting mixture was evaporated to a thick, green paste, then dried over night at about 110° C. The resulting green material was calcined for two hours at 380° C. The final product was a hard, light green material which was ground to a 10-30 mesh. The results are reported in Table 1.

EXAMPLE 3

The procedure of Example 1 was repeated except that a catalyst of the composition 30% $Mo_5SnO_x$, 52.5% $SiO_2$, 17.5% $Al_2O_3$ was used. The catalyst was prepared by dissolving 35.1 g of molybdenum trioxide in the form of ammonium heptamolybdate in 700 cc of distilled water to yield a clear solution. To this solution was added 6.0 g of stannic oxide, the resulting slurry was then boiled for about one-half hour, after which 148.4 g of 41% Nalco silica sol and 20.2 g of Dispal M alumina were added. The resulting mixture was evaporated to a thick, white paste, then dried over night at about 110° C. The resulting white material was calcined for two hours at 380° C. The final product was a hard, light blue material which was ground to a 10-30 mesh. The results are reported in Table 1.

EXAMPLE 4

The procedure of Example 1 was repeated except that a catalyst of the composition 30% $Cu_4SnO_x$, 52.5% $SiO_2$, 17.5% $Al_2O_3$ was used. The catalyst was prepared by dissolving 39.9 g of $Cu(CH_3COO)_2H_2O$ in 700 cc of distilled water to yield a clear blue solution. To this solution was added 7.5 g of stannic oxide to yield a light blue slurry. The mixture was then boiled for about one-half hour, after which 99.2 g of 41% Nalco silica sol and 13.6 g of Dispal M alumina were added. The resulting mixture was evaporated to a thick, light blue paste, then dried over night at about 110° C. The resulting light blue material was calcined for two hours at 380° C. The final product was soft, dark blue material which was ground to a 10-30 mesh. The results are reported in Table 1.

EXAMPLE 5

The procedure of Example 1 was repeated except that a catalyst of the composition 30% $MoO_x$, 52.5% $SiO_2$, 17.5% $Al_2O_3$ was used. The catalyst was prepared by dissolving 30 g of molybdenum trioxide in the form of ammonium heptamolybdate in 800 cc of distilled water to yield a clear solution. The solution was boiled for about ½ hour after which 128.0 g of 41% Nalco silica sol and 17.5 g of Dispal M alumina were added. The resulting mixture was evaporated to a thick white paste, then dried overnight at 110° C. The resulting white material was calcined for two hours at 380° C. The final product was a hard material which was ground to 10-30 mesh. The results are reported in Table 1.

EXAMPLE 6

The procedure of Example 1 was repeated except that a catalyst of the composition 30% $CuO_x$, 52.5% $SiO_2$, 17.5% $Al_2O_3$ was used. The catalyst was prepared by dissolving 75.3 g of $Cu(CH_3COO)_2H_2O$ in 700 cc of distilled water to yield a clear blue solution. The solution was then boiled for ½ hour after which 128.0 g of 41% Nalco silica sol and 17.5 g of Dispal M alumina were added. The resulting mixture was evaporated to a thick, dark blue paste and then dried overnight at 110° C. The resulting material was calcined for two hours at 380° C. The final product was a soft, dark blue material which was ground to 10-30 mesh. The results are reported in Table 1.

EXAMPLE 7

The procedure of Example 1 was repeated except that a catalyst of the composition 30% $SnO_x$, 52.5% $SiO_2$, 17.5% $Al_2O_3$ was used. The catalyst was prepared by dispersing 30.0 g of $SnO_2$ in 700 cc of distilled water. The dispersion was then boiled for ½ hour after which 128.0 g of 41% Nalco silica sol and 17.5 g of Dispal M alumina were added. The resulting mixture was evaporated to a thick, white paste and then dried at 110° C. The resulting material was calcined for two hours at 380° C. The final product was a hard, white mateial which was ground to 10–30 mesh. The results are reported in Table 1.

COMPARATIVE EXAMPLE A

The procedure of Example 1 was repeated except no catalyst was used. The reactor was packed with Alundum particles. The results are reported in Table 1.

TABLE 1

| | | Lactic acid to Propanoic, Acetic Acid, and Acetaldehyde | | | | | | |
|---|---|---|---|---|---|---|---|---|
| Ex No | Catalyst Composition** | Propanioc Acid | | Acetic Acid | | Acetaldehyde | | Total Conver. |
| | | PPC | Selectivity* | PPC | Selectivity* | PPC | Selectivity* | |
| 1 | $Mo_5Cu_4SnO_x$ | 64.3 | 64.9 | 0 | 0 | 8.5 | 12.8 | 99.1 |
| 2 | $Mo_5Cu_4O_x$ | 6.2 | 6.3 | 26.2 | 40.4 | 28.2 | 43.5 | 97.1 |
| 3 | $Mo_5SnO_x$ | 13.6 | 14.6 | 25.1 | 40.7 | 17.9 | 28.9 | 92.7 |
| 4 | $Cu_4SnO_x$ | 0 | 0 | 46.9 | 71.8 | 6.4 | 9.8 | 98.0 |
| 5 | $MoO_x$ | 21.0 | 22.8 | 19.8 | 32.1 | 16.8 | 27.2 | 92.4 |
| 6 | $CuO_x$ | 2.4 | 2.5 | 37.6 | 58.0 | 8.2 | 12.6 | 97.3 |
| 7 | $SnO_x$ | 1.93 | 2.1 | 5.5 | 8.9 | 43.4 | 71.0 | 91.7 |
| A | — | 10.6 | 28.6 | 5.6 | 22.7 | 4.2 | 17.1 | 37.1 |

*Based on theoretical 100%
**All catalysts were composed of 30% of the active material indicated above, 52.5% $SiO_2$ and 17.5% $Al_2O_3$ Although the invention has been described in detail through the preceeding examples, these examples are for the purpose of illustration only and it is understood that variations and modifications can be made by one skilled in the art without departing from the spirit and scope of the invention:

We claim:

1. A process for the conversion of an alpha-hydroxycarboxylic acid of the formula:

R—CHOH—COOH wherein
R is hydrogen or an alkyl having from 1 to 4 carbon atoms, to hydroxy free aliphatic caboxylic acids and aldehydes which process comprises contacting the alpha-hydroxycarboxylic with a solid catalyst of the formula:

$$M_aM'_bO_x$$

wherein
M is at least one element selected from molybdenum, copper, tin or a combination thereof; and
M' is at least one of an element selected from Group IA, IIA, IVA, VA VIA, VIIIB, VB;
with the proviso that when M is selected from Group IVA then M' is not tin; and
a is 0.1 to 1;
b is 0.0 to 0.5; and
x is a number sufficient to satisfy the valence requirements of the other elements present,
and at a temperature between about 200 degrees C. to about 600 degrees C.

2. The process of claim 1 wherein the α-hydroxycarboxylic acid is lactic acid.

3. The process of claim 2 wherein M' is Na, K, Rb, Mg, Ca, P, Sb, Bi, Te, Ge, Sn, Pb, Fe, Co, Ni, V, or Nb.

4. The process of claim 2 conducted in the vapor phase and in the presence of a diluent gas.

5. The process of claim 4 wherein the diluent gas is steam or nitrogen.

6. The process of claim 2 wherein the catalyst is supported on a carrier of silica-alumina, silica, alumina, titania, or zirconia.

7. The process of claim 6 wherein the catalyst is supported on a carrier of silica-alumina.

* * * * *